United States Patent [19]

Sale et al.

[11] 4,007,276
[45] Feb. 8, 1977

[54] TRIAZOLO ISOINDOLE DERIVATIVES

[75] Inventors: Amedeo Omodei Sale, Voghera (Pavia); Pietro Consonni; Leonard J. Lerner, both of Milan, all of Italy

[73] Assignee: Gruppo Lepetit, S.p.A., Milan, Italy

[22] Filed: May 10, 1976

[21] Appl. No.: 684,592

Related U.S. Application Data

[63] Continuation-in-part of Ser. No. 473,256, May 24, 1974, abandoned.

[30] Foreign Application Priority Data

May 25, 1973 United Kingdom ............ 25163/73

[52] U.S. Cl. .............................. 424/263; 424/269; 260/296 T; 260/308 R
[51] Int. Cl.² ...................................... C07D 249/16
[58] Field of Search .................. 260/296 T, 308 R; 424/263, 269

[56] References Cited

OTHER PUBLICATIONS

Chemical Abstracts, Eighth Collective Index, p. 31865S.
Chemical Abstracts, vol. 82, Chemical Substance Index, p. 4392 CS, (1975).
Singh et al, J. Am. Chem. Soc., vol. 91, pp. 3670–3671 (1969).
Kersten et al, Makromol. Chem., vol. 138, pp. 265–278 (1970).
Alaimo, J. Heterocycl. Chem., 1973, pp. 769–772.

*Primary Examiner*—John D. Randolph
*Attorney, Agent, or Firm*—Theodore Post; C. Kenneth Bjork

[57] ABSTRACT

New s-triazolo[5,1-a]isoindole derivatives of following formula I

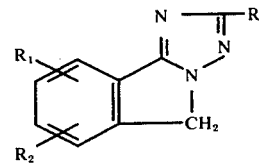

wherein R is selected from hydrogen, amino, lower alkyl amino, di-lower alkyl amino, acylamino, diacylamino, benzoylamino, ureido, thioureido, carbethoxythioureido, benzoylthioureido, sulfhydryl, lower alkyl, trifluoromethyl, phenyl, substituted phenyl, pyridyl, methylpyridyl and dimethylpyridyl; and $R_1$ and $R_2$ each independently represents hydrogen, chloro or lower alkoxy.

A process for their manufacture which comprises the reaction of 2-aminophthalimidine with a reagent R-Z wherein R has the same meaning as above, and Z represents one of the following groups:

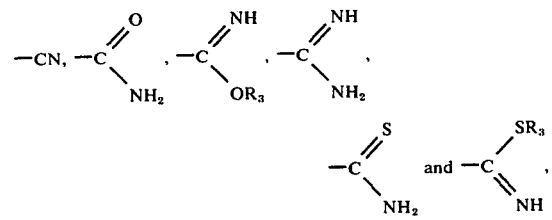

wherein $R_3$ is $C_1$–$C_4$ alkyl.

The compounds and some of the intermediates of the process are useful as antiinflammatories, analgesics, CNS depressants, antimicrobials and anti-fertility agents.

18 Claims, No Drawings

TRIAZOLO ISOINDOLE DERIVATIVES

CROSS REFERENCE TO RELATED APPLICATION

This application is a continuation-in-part of U.S. Patent application Ser. No. 473,256, filed May 24, 1974, now abandoned.

SUMMARY OF THE INVENTION

This invention relates to new s-triazolo isoindole derivatives of following formula I and a process for their manufacture

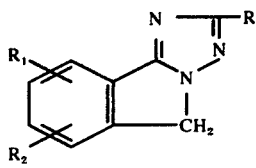   I

In the formula, R is selected from hydrogen, amino, lower alkyl amino, di-lower alkyl amino, lower alkanoylamino, di-lower alkanoylamino, benzoylamino, ureido, thioureido, carbethoxythioureido, benzoylthioureido, sulfhydryl, lower alkyl, trifluoromethyl, phenyl, substituted phenyl, pyridyl, methylpyridyl and dimethylpyridyl; and $R_1$ and $R_2$ each independently represents hydrogen, chloro or lower alkoxy.

In the specification and claims, the term and the portion "lower alkanoyl" identifies lower alkanoyl radicals derived from an alkanoic acid of 1 to 6 carbon atoms, e.g. formyl, acetyl, propionyl, butyryl, isobutyryl, pentanoyl, pivaloyl and hexanoyl.

The term "substituted phenyl" identifies a phenyl radical which carries one to three substituents independently selected from lower alkyl, lower alkoxy, lower alkenyloxy, lower alkynyloxy, methylenedioxy, halo, trifluoromethyl, hydroxy, cyclopropyloxy, cyclobutyloxy, cyclopentyloxy, cyclohexyloxy, benzyloxy, carboxymethoxy, carbo(lower alkoxy)methoxy, amino, lower alkylamino, di-lower alkylamino, lower alkanoylamino, benzoylamino and nitro.

The term "lower alkyl" and the portion "lower alkyl" in the term "lower alkylamino" identify a branched or linear alkyl radical containing from 1 to 5 carbon atoms, such as methyl, ethyl, propyl, butyl, isobutyl, tert.-butyl, pentyl and neopentyl.

The term "lower alkoxy" designates a branched or linear 1 to 5 carbon atom alkoxy group, e.g., methoxy, ethoxy, propoxy, isopropoxy, isobutoxy, tert.-butoxy, pentyloxy, isoamyloxy, 2-methylbutoxy or neopentyloxy.

The term "lower alkenyloxy" identifies a branched or linear 3 to 5 carbon atom alkenyloxy group, e.g., allyloxy, 2-butenyloxy, 1-methyl-2-propenyloxy, 1,1-dimethyl-2-propenyloxy, 3-methyl-2-butenyloxy, 2-pentenyloxy, 3-pentenyloxy or 4-pentenyloxy.

The term "lower alkynyloxy" identifies a branched or linear 3 to 5 carbon atom alkynyloxy group, e.g., propargyloxy, 2-butynyloxy, 1-methyl-2-propynyloxy, 1,1-dimethyl-2-propynyloxy, 2-pentynyloxy, 3-pentynyloxy or 4-pentynyloxy.

The term "halo" designates chloro, bromo or fluoro.

The compounds of this invention are useful as CNS depressants, analgesics, antiinflammatories, antimicrobials and as anti-fertility agents.

A preferred group of compounds comprises those compounds of formula I wherein R is a phenyl or a substituted phenyl of the formula

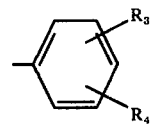

wherein one of the substituents $R_3$ and $R_4$ is located in the 3- or 4-position of the phenyl radical and represents a lower alkyl, lower alkoxy, lower alkenyloxy, lower alkynyloxy, di-lower alkylamino, halo, trifluoromethyl, hydroxy, cyclopropyloxy, cyclobutyloxy, cyclopentyloxy, cyclohexyloxy or benzyloxy group and the other is hydrogen, lower alkoxy or halo; or $R_3$ and $R_4$ taken together represent methylenedioxy; and $R_1$ and $R_2$ have the same meanings as before. This group of compounds shows a remarkable anti-fertility utility.

A second group of preferred compounds comprises those compounds of formula I wherein R is a lower alkyl, lower alkylamino, di-lower alkylamino, lower alkanoylamino, di-lower alkanoylamino, benzoylamino, ureido or sulfhydryl group; and $R_1$ and $R_2$ have the same meanings as before and preferably are both hydrogen. Representative members of this group of compounds show anti-inflammatory utility.

The compounds wherein R is an amino or a lower alkyl group also have CNS depressant utility.

A third group of preferred compounds comprises those compounds wherein R is pyridyl, methylpyridyl or dimethylpyridyl; $R_1$ and $R_2$ have the same meanings as given before and most preferably are both hydrogen. Representative members of this group show CNS depressant utility.

A further group of preferred compounds comprises those compounds wherein R is thioureido or carbethoxythioureido, $R_1$ and $R_2$ have the same meanings as given before, and most preferably are both hydrogen. Representative members of this group show antimicrobial activity.

The process for preparing the new compounds of this invention is indicated by the following scheme:

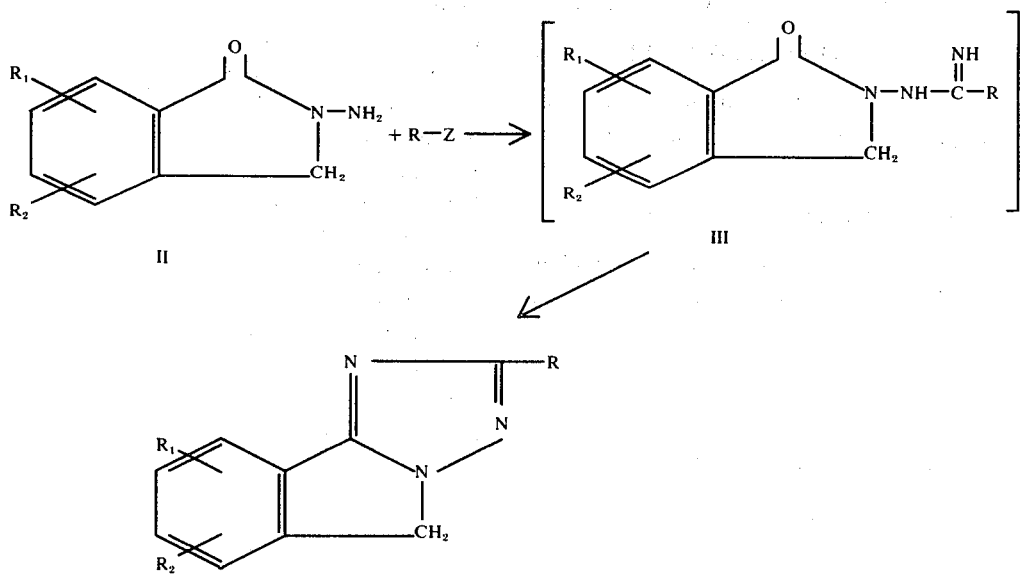

wherein R and $R_1$ have the same meanings as above, and Z represents one of the following groups:

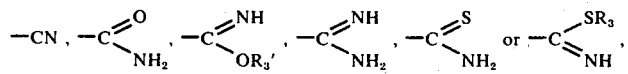

wherein $R_3$ and $C_1$–$C_4$ alkyl. Both reactants may be used as free compounds or as their corresponding acid or basic salts. For instance, the compound II may be utilized in the form of its hydrochloride, while the compound R-Z, when representing thiocyanic acid, i.e. HSCN, may be employed in the form of one of its salts with an alkali metal, or when R-Z is an imidoether, it may be used in the form of its hydrochloride.

In practice, the reaction is effected in two steps, but the isolation of intermediate III is not strictly necessary. However, in some cases it is preferred to isolate and characterize the open chain derivative III, since some of these compounds have interesting utilities as anti-inflammatories, analgesics and CNS depressants. A particular group of compounds of formula III which exhibit remarkable pharmacological utilities of the before-mentioned types comprises those derivatives where R is phenyl or substituted phenyl, as defined above.

The first condensation step is carried out by treating for 3 to 30 hours at a temperature ranging from about 60° to about 160° C the N-aminophthalimidine II with a compound of formula R-Z. Although the proportions of the reactants are not strictly critical, in most cases an excess of the latter reactant is employed to obtain higher yields.

Small amounts of an acidic substance catalyze the condensation reaction. Generally, the acidic catalyst consists of a hydrohalide which is introduced in the reaction mixture, and when it is possible, said hydrohalide catalyst is employed as a hydrohalide salt of the reactant R-Z. For instance, in a practical example, the first step of the reaction is effected by heating one molecular proportion of N-aminophthalimidine II with about 1.5 molecular proportions of the ethyl ester of m-chlorobenzimidic acid and 0.1 molecular proportion of the hydrochloride of said ester. The compound resulting from such condensation is N-(m-chlorobenzimidoylamino)phthalimidine of formula III.

To complete the reaction according to the given scheme, the obtained mixture containing the intermediate III is dissolved in a solvent such as a lower alkanol and, after addition of a basic catalyst, for instance, of about 0.5 molecular proportion of a strong base such as sodium hydride or an alkali metal lower alkoxide, is refluxed for 3 to 8 hours.

The final product I is then recovered according to usual procedures, for example, by evaporating the reaction solvent, dissolving the resulting crude solid in a water immiscible organic solvent, washing with water, evaporating off the organic phase and purifying the product by crystallization or column chromatography.

If it is desired to isolate the intermediate III, the mixture derived from the first reaction step is washed with aqueous sodium bicarbonate and water and the resulting crude product is purified by crystallization from a suitable solvent.

The reactants of formula II which may be employed according to the given scheme are prepared according to procedures described by E. Bellasio et al., Annali di Chimica, 59, 451, 1969. These procedures involve rearrangement of tetrahydrophthalazin-1-ones or their 3-acetyl derivatives by means of phosphorous pentachloride or hydrazine. This rearrangement may also be promoted by boiling with a strong acid such as 20% hydrochloric acid or a base such as an alkali metal hydroxide. The tetrahydrophthalazin-1-ones are obtained by reduction of the corresponding 2-acetyl-1(2H)-phthalazinones with zinc in 70% acetic acid or by catalytic hydrogenation; E. Bellasio et al., Annali di Chimica, 59, 443, 1969.

As the starting compounds R-Z, there are preferably employed an imidate, a cyanamide, a cyanic acid or a thiocyanic acid derivative.

Some compounds of formula I may be obtained also through chemical modification of other compounds falling within the scope of formula I prepared according to the reaction scheme outlined before. For instance, compounds I were R is lower alkanoylamino, di-lower alkanoylamino or benzoylamino are prepared by acylation of the corresponding derivatives where R is amino. Compounds of formula I where R is lower alkylamino are prepared by reduction of the corresponding alkanoylamino or aldimino derivative with lithium aluminum hydride. Catalytic hydrogenation of a mixture of a compound of formula I wherein R is amino with an excess of a lower aliphatic aldehyde affords a compound of formula II wherein R is di-lower alkylamino. Compounds where R is thioureido are prepared by hydrolytic cleavage (e.g. by boiling in dilute sodium hydroxide) of the corresponding carbethoxy- or benzoyl-thioureido derivative which, in turn, is obtained from the 2-amino derivative and carbethoxy- or benzoylisothiocyanate. Desulfurization of the thioureido derivative (e.g. with $H_2O_2$ and alkali) leads to the corresponding ureido derivative.

Compounds of formula I where R is hydrogen are also prepared from the corresponding derivative where R is amino by treatment with sodium nitrite in acidic medium followed by reduction with $H_3PO_2$. The compound wherein R is hydroxyphenyl may also be prepared by hydrogenolysis of the corresponding benzyloxyphenyl derivative. Accordingly, the compounds wherein R is phenyl substituted with lower alkyloxy, lower alkenyloxy, lower alkynyloxy, cyclopropyloxy, cyclobutyloxy, cyclopentyloxy or cyclohexyloxy, may also be prepared by reaction of the hydroxyphenyl derivative with a suitable alkylating agent such as a lower alkyl, lower alkenyl, lower alkynyl, cyclopropyl, cyclobutyl, cyclopentyl or cyclohexyl halide or the corresponding tosylate or mesylate. Moreover, by reacting compounds of formula I wherein R is hydroxyphenyl with an α-haloacetic acid or its lower alkyl ester in the presence of an acid acceptor, the corresponding compound wherein R is carboxymethoxy-phenyl or carbo(lower alkoxy)methoxy-phenyl is obtained.

The compounds wherein R is aminophenyl, lower alkylamino-phenyl, di-lower alkylamino-phenyl and acylaminophenyl may in turn be obtained from the corresponding nitro derivatives through catalytic hydrogenation followed by the usual alkylation and acylation procedures.

Another suitable method for preparing the compounds of formula I wherein R is phenyl or substituted phenyl and $R_1$ and $R_2$ have the same meaning as before consists in cyclizing s-triazole derivatives of formula IV according to the following scheme:

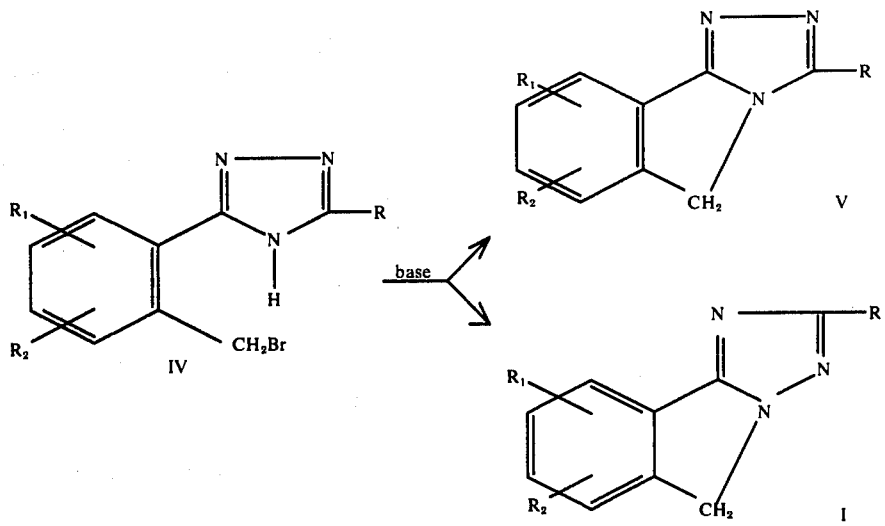

wherein R is phenyl or substituted phenyl.

The starting triazoles of formula IV are prepared according to the same procedure described in Belgian Patent 780,885 for the homolog 1-methyl-3-phenyl-5-(2-bromomethylphenyl)-1,2,4-triazole. The cyclization reaction is carried out by refluxing the compounds of formula IV in a lower alkanol in the presence of a strong base such as, for example, sodium amide, sodium hydride or sodium ethoxide. The mixture of the two isomeric compounds of formulas V and I which forms according to the reaction scheme, contains a higher percentage of the isomer of formula I which is separated from that of formula V by extraction of the solid mixture with solvents.

The anti-inflammatory activity of some representative compounds of formula I as hereinbefore described was evidenced by means of the carrageenin tests in rats. This test is carried out in the hind paw of the rat which paw has been inflammed by injection of carrageenin according to the technique described by C.A. Winter and coworker, Proc. Soc. Exptl. Biol. Med. III, 554 (1962). In following Table I are reported the percent inhibition of the carrageenin induced edema at the dose level indicated for each compound.

TABLE I

| Compound | Dose Level mg/Kg p.o. | Per Cent Inhibition of the Edema |
|---|---|---|
| a | 100 | 28 |
| b | 100 | 50 |
|   | 50 | 38 |
| c | 100 | 54 |
|   | 50 | 35 |
| d | 100 | 53 |
|   | 50 | 34 |
| e | 100 | 29 |
| f | 100 | 28 |
| g | 100 | 49 |

TABLE I-continued

| Compound | Dose Level mg/Kg p.o. | Per Cent Inhibition of the Edema |
|---|---|---|
| | 50 | 39 | a): 2-n-butyl-5H-s-triazolo[5,1-a]isoindole
b): 2-dimethylamino-5H-s-triazolo[5,1-a]isoindole
c): 2-acetamido-5H-s-triazolo[5,1-a]isoindole
d): 2-diacetylamino-5H-s-triazolo[5,1-a]isoindole
e): 2-ureido-5H-s-triazolo[5,1-a]isoindole
f): 2-benzoylamino-5H-s-triazolo[5,1-a]isoindole
g): 2-sulfhydryl-5H-s-triazolo[5,1-a]isoindole The CNS depressant properties of compounds hereinbefore described were investigated according to the Irwin method and in particular the anti-anxiety effect was evaluated on the basis of the secondary conditioned avoidance response test. A specific anti-anxiety effect was evidenced by administering to conditioned rats doses of 15–60 mg/kg i.p. of representative said compounds of the invention.

Following Table II indicates the ratio of the rats which are deconditioned after administration of predetermined amounts of said representative compounds:

TABLE II

| Compound | Dose mg/kg i.p. | Deconditioned treated | Toxicity $LD_{50}$ mg/kg i.p. in mice |
|---|---|---|---|
| 2-Amino-5H-s-triazolo[5,1-a]-isoindole | 30 | 8/10 | 600 |
| 2-Methyl-5H-s-triazolo[5,1-a]isoindole | 30 | 7/10 | >400 |
| | 15 | 6/10 | |

In evaluating the antimicrobial utility of representative compounds as hereinbefore described, the minimal concentration of substance inhibiting bacterial growth (M.I.C.=minimal inhibitory concentration) was determined. The compounds 2-carbethoxythioureido-5H-s-triazolo[5,1-a isoindole showed an M.I.C. of 5 μg per milliliter against *Mycobacterium tubercolosis* $H_{37}Rv$.

The analgesic activity of representative compounds as hereinbefore described was assessed in rats by following essentially the procedure described by L. O. Randall and J. J. Selitto, Arch. Int. Pharmacodyn., 111, 409 (1957). The compound 2-(3-pyridyl)-5H-s-triazolo[5,1-a isoindole at a dose of 50 mg/kg i.p. increases by 70 percent the pain threshold of the rats without provoking any toxic effect.

A particular group of compounds of this invention comprises those derivatives of formula I as hereinbefore described which are useful as anti-fertility agents. These compounds show this utility when administered to laboratory animals, e.g. rats, hamsters, dogs and monkeys. Moreover, the anti-fertility activity of these new compounds is not associated with other biological effects which are usual with known hormonal substances.

Fertility regulation can usually be achieved in a number of ways through the administration of hormonal substances. These can involve ovulation inhibition, ova transport, fertilization, implantation of the zygote, resorption of the fetus or abortion. Only with ovulation inhibition has there developed a successful method that is clinically useful.

The compounds of this invention which pertain to the group identified above allow an entirely new approach to this problem in which a non-hormonal compound can be administered parenterally or orally on a once or more times per month basis or as needed for a "missed period" or to induce termination of a more advanced pregenancy.

Representative experiments for assessing anti-fertility activity are carried out with female Sprague-Dawley rats weighing 200–230 g. They were mated with proven fertile males. The presence of sperm in the vagina of these animals is evidence of mating and is also considered as being day one of pregnancy. Pregnancy is confirmed at the time of autopsy by the presence of fetuses or implantation sites in the uterus. Even when animals abort the fetuses, implantation scars remain as evidence that the animal had been pregnant.

The test compounds dissolved or suspended in sesame oil were administered subcutaneously at doses of 5 mg/kg daily for 5 consecutive days beginning on day 6 of pregnancy (days 6–10). These animals were autopsied on day 16 of pregnancy and the uteri were examined for evidence of pregnancy and termination of pregnancy such as implantation sites, live or resorbing fetuses and hemorrage as well as abnormalities of the uterus, placenta or fetuses. A compound is considered to be active if there is a reduction of live fetuses in at least 60% of the treated animals and the presence of implantation sites proves the animals to have been pregnant. In representative experiments the following compounds proved to be active according to the above mentioned criteria:

2-Phenyl-5H-s-triazolo[5,1-a]isoindole
2-(m-Methoxyphenyl)-5H-s-triazolo[5,1-a]isoindole
2-(m-Ethoxyphenyl)-5H-s-triazolo[5,1-a]isoindole
2-(m-Propoxyphenyl)-5H-s-triazolo[5,1-a]isoindole
2-m-Benzyloxyphenyl)-5H-s-triazolo[5,1-a]isoindole
2-(3,4-Methylenedioxyphenyl)-5H-s-triazolo[5,1-a]isoindole
2-(p-Chlorophenyl)-5H-s-triazolo[5,1-a]isoindole
2-(p-Methoxyphenyl)-5H-s-triazolo[5,1-a]isoindole
2-(m-Tolyl)-5H-s-triazolo[5,1-a]isoindole
2-(m-Chlorophenyl)-5H-s-triazolo[5,1-a]isoindole
2-(m-Hydroxyphenyl)-5H-s-triazolo[5,1-a]isoindole
2-(m-Dimethylaminophenyl)-5H-s-triazolo[5,1-a]isoindole
8-Chloro-2-phenyl-5H-s-triazolo[5,1-a]isoindole
8-Chloro-2-(m-methoxyphenyl)-5H-s-triazolo[5,1-a]isoindole
7-Chloro-2-phenyl-5H-s-triazolo[5,1-a]isoindole
7-Chloro-2-(m-methoxyphenyl)-5H-s-triazolo[5,1-a]isoindole
8-Methoxy-2-phenyl-5H-s-triazolo[5,1-a]isoindole
8-Methoxy-2-(m-methoxyphenyl)-5H-s-triazolo[5,1-a]isoindole Those compounds that demonstrated 100% effectiveness, i.e., an absence of live fetuses in 100% of the animals, and had minimal side effects or toxicity were studied further.

The following Table III shows the typical dose responses of several of these highly effective anti-fertility compounds.

TABLE III

| Compound | Dose mg/kg/day S.C. | No. of Rats | % Animals Aborting | |
|---|---|---|---|---|
| 2-Phenyl-5H-s-triazolo[5-1-a]-isoindole | 2.5 | 5 | 80 | |
|  | 1.25 | 5 | 20 | |
| 2-(m-Methoxyphenyl)-5H-s-triazolo[5,1-a]-isoindole | 5 | 19 | 100 | |
|  | 2.5 | 13 | 100 | |
|  | 1.25 | 24 | 70.8 | |
|  | 0.62 | 13 | 38.5 | |
|  | 0.31 | 11 | 0 | |
|  | 0.155 | 5 | 0 | |
| 2-(m-Ethoxyphenyl)-5H-s-triazolo[5,1-a]-isoindole | 5 | 5 | 100 | |
|  | 2.5 | 7 | 85.7 | |
|  | 1.25 | 8 | 62.5 | |
|  | 1 | 6 | 33.3 | |
| 2-(m-Propoxyphenyl)-5H-s-triazolo[5,1-a]-isoindole | 5 | 6 | 100 | |
|  | 2.5 | 9 | 77.8 | |
|  | 1.25 | 5 | 60 | |
|  | 1 | 5 | 20 | |
| 2-(3,4-Methylenedioxyphenyl)-5H-s-triazolo[5,1-a]-isoindole | 5 | 5 | 100 | |
|  | 2.5 | 9 | 66.7 | |
|  | 1.25 | 4 | 25 | |
|  | 1 | 4 | 0 | |
| 8-Methoxy-2-(m-methoxyphenyl)-5H-s-triazolo-[5,1-a]isoindole | 5 | 4 | 100 | |
|  | 2.5 | 7 | 57.1 | |
| Vehicle | — | 21 | 0 | (contained 95% live fetuses) |

The anti-fertility activity of these compounds in rats was also confirmed in other species including mice, hamsters, rabbits, dogs, monkeys and baboons. With hamsters, the same criteria and conditions are followed as for testing in rats, with the exception that the animals (female Syrian golden hamsters weighing 100 to 130 g) are treated on day 4 through day 8 with 5 mg/kg s.c. of the test compound and are autopsied on day 14 of pregnancy. Under these experimental conditions, the following compounds either eliminated or severely reduced the number of live fetuses in at least 60% of the treated animals:

2-Phenyl-5H-s-triazolo[5,1-a]isoindole
2-(m-Chlorophenyl)-5H-s-triazolo[5,1-a]isoindole
2-(p-Chlorophenyl)-5H-s-triazolo[5,1-a]isoindole
2-(m-Fluorophenyl)-5H-s-triazolo[5,1-a]isoindole
2-(p-Fluorophenyl)-5H-s-triazolo[5,1-a]isoindole
2-(m-Tolyl)-5H-s-triazolo[5,1-a]isoindole
2-(p-Tolyl)-5H-s-triazolo[5,1-a]isoindole
2-(m-Trifluoromethylphenyl)-5H-s-triazolo[5,1-a]isoindole
2-(m-Dimethylaminophenyl)-5H-s-triazolo[5,1-a]isoindole
2-(m-Hydroxyphenyl)-5H-s-triazolo[5,1-a]isoindole
2-(m-Methoxyphenyl)-5H-s-triazolo[5,1-a]isoindole
2-(m-Ethoxyphenyl)-5H-s-triazolo[5,1-a]isoindole
2-(m-Propoxyphenyl)-5H-s-triazolo[5,1-a]isoindole
2-(m-Benzyloxyphenyl)-5H-s-triazolo[5,1-a]isoindole
2-(p-Methoxyphenyl)-5H-s-triazolo[5,1-a]isoindole
2-(3,4-Methylenedioxyphenyl)-5H-s-triazolo[5,1-a]isoindole
7-Chloro-2-phenyl-5H-s-triazolo[5,1-a]isoindole
2-(m-Methoxyphenyl)-7-chloro-5H-s-triazolo[5,1-a]isoindole
8-Chloro-2-phenyl-5H-s-triazolo[5,1-a]isoindole
8Chloro-2-(m-methoxyphenyl)-5H-s-triazolo[5,1-a]isoindole
2-(m-Methoxyphenyl)-7-methoxy-5H-s-triazolo[5,1-a]isoindole
2-Phenyl-8-methoxy-5H-s-triazolo[5,1-a]isoindole
2-(m-Methoxyphenyl)-8-methoxy-5H-s-triazolo[5,1-a]isoindole
7,8-Dimethoxyphenyl-2-(m-methoxyphenyl)-5H-s-triazolo[5,1-a]isoindole When tested in baboons, the compound, 2-(m-Methoxyphenyl)- 5H-s-triazolo[5,1-a]isoindole, induced abortion in every animal studied.

The compounds of formula I have very low toxicity, since generally their $LD_{50}$ values in mice are higher than 400 mg/kg i.p., and are well tolerated at the biologically active dosages. The compounds of the invention may be administered by various routes, for example, orally, subcutaneously, intravenously or intramuscularly. For oral administration the substances are compounded in such forms as tablets, dispersible powders, capsules, granules, syrups, elixirs, and solutions. The compositions for oral use may contain one or more conventional adjuvants, such as, for instance, sweetening agents, flavoring agents, coloring agents and coating and preservative agents, in order to provide an elegant and palatable preparation. Tablets may contain the active ingredient admixed with conventional pharmaceutically acceptable excipient, e.g., inert diluents such as calcium carbonate, sodium carbonate, lactose and talc; granulating and disintegrating agents, such as, for instance, starch, alginic acid and sodium carboxymethylcellulose; binding agents, e.g., starch, gelatin, gum arabic and polyvinylpyrrolidone; and lubricating agents, e.g. magnesium stearate, stearic acid and talc. The tablets may be uncoated or coated by known techniques to delay disintegration and absorption in the gastrointestinal tract in order to provide long acting compositions. Syrups, elixirs and solutions are formulated as known in the art. Together with the active compound they may contain suspending agents, such as, for instance, methylcellulose, hydroxyethylcellulose, tragacanth and sodium alginate, wetting agents, e.g., lecithin, polyoxyethylene stearates and polyoxyethylene sorbitan monooleate, and the common preservative, sweetening and buffering agents. A capsule or a tablet may contain the active ingredient alone or admixed with an inert solid diluent, such as, for instance calcium carbonate, calcium phosphate and kaolin.

Besides the oral route, other useful ways for administering the compounds of the invention may be suitably employed, such as, for instance, the intravenous or the intramuscular route. The active ingredient is thus embodied in injectable dosage forms. Such compositions are formulated according to ways known to the art skilled and may contain appropriate dispersing or wetting agents and suspending or buffering agents identical or similar to those mentioned above. Sesame oil, benzyl alcohol, benzyl benzoate, peanut oil and their mixtures may be suitably employed as vehicles when the compounds are slightly soluble in aqueous media.

The compounds of the invention may also be administered in the form of their nontoxic pharmaceutically acceptable acid addition salts. Such salts possess the same degree of activity as the free bases, from which they are readily prepared by reacting the base with an appropriate acid and, accordingly, are included within the scope of the invention. Represenative of such salts are the mineral acid salts, such as, for instance, the hydrochloride, hydrobromide, sulfate, phosphate and the like and the organic acid salts such as, for example, the succinate, benzoate, p-toluenesulfonate, benzene sulfonate, maleate, tartrate, methanesulfonate, cyclohexylsulfonate and the like.

The dosage of active ingredient employed for combatting inflammatory or anxious states in mammals, or for inhibiting reproduction, will vary depending upon the compound employed and the severity of the condition being treated. Generally, good results are obtained when compounds of the above formulas I and III are administered at a daily dosage of from about 0.8 to about 50 mg/kg of animal body weight. The dosage forms useful for this purpose generally contain from about 10 to about 600 mg of the active ingredient in admixture with a solid or liquid pharmaceutically-acceptable carrier or diluent.

DESCRIPTION OF SOME PREFERRED EMBODIMENTS

The following examples further illustrate the invention and describe in detail some compounds of the general formulas I and III without limiting th scope of the invention.

EXAMPLE 1

2-(p-Tolyl)-5H-s-triazolo[5,1-a]isoindole

A mixture of 8.83 g of N-aminophthalimidine (0.06 mole), 12.75 g of p-toluimidic acid ethyl ester (0.078 mole) and 2.4 g of the hydrochloride of p-toluimidic acid ethyl ester (0.012 mole) is heated under vacuum (200 mm Hg) fpr five hours at about 90°C and for two hours at about 125°C. Then 1.95 g of p-toluimidic acid ethyl ester (0.012 mole) is added and the mixture is heated for a further 16 hours at about 125–6°C under vacuum. All volatile materials are eliminated by distilling off at 125°C and 5 mm Hg. The solid residue may be used as such for the cyclization step or, after washing with aqueous sodium bicarbonate and water, may be purified by crystallization from ethyl acetate to isolate the intermediate of formula III, 2-(p-toluimidoylamino)phthalimidine (M.p. 210–11°C).

The crude reaction product is cyclized by heating for five hours in 95 ml of ethanol containing 0.72 g of 80% sodium hydride (0.024 mole). The reaction mixture is then evaporated to dryness in vacuo and dissolved in dichloromethane. The organic solution, after washing with water, is evaporated and the crude residual compound is crystallized from 70% ethanol, yielding 10.2 g (69%) of the title compound. M.p. 207–8°C. The cyclization of the purified intermediate of formula III may be effected according to the same procedure as above.

EXAMPLES 2–25

By reacting N-aminophthalimidine with the imidic acid ethyl esters identified under column A in the presence of its hydrochloride, essentially according to the procedure of Example 1, the 5H-s-triazolo[5,1-a]isoindole identified under column B is obtained. The melting points (or boiling points) of the corresponding imidoylaminophthalimidine intermediates, when isolated, are aldo reported.

| Example No. | A imidic acid ethyl ester | B -5H-s-triazolo [5,1-a]isoindole | M.p. ° C | Overall Yield, % | M.p. of the intermediates, ° C |
|---|---|---|---|---|---|
| 2 | m-toluimidic | 2-(m-tolyl) | 174–5 | 75 | 158–60 |
| 3 | o-toluimidic | 2-(o-tolyl) | 125–6 | 39 | |
| 4 | benzimidic | 2-phenyl | 159–60 | 77 | 207–8 |
| 5 | m-methoxybenzimidic | 2-(m-methoxyphenyl) | 132–3 | 63 | 157–8 |
| 6 | o-chlorobenzimidic | 2-(o-chlorophenyl) | 167–8 | 43 | |
| 7 | m-chlorobenzimidic | 2-(m-chlorophenyl) | 221 | 76 | 211–2 |
| 8 | p-chlorobenzimidic | 2-(p-chlorophenyl) | 247–8 | 82 | |
| 9 | acetimidic | 2-methyl | 117–8 | 67 | |
| 10 | nicotinimidic | 2-(3-pyridyl) | 162–3 | 75 | |
| 11 | 3,4,5-trimethoxy-benzimidic | 2-(3,4,5-trimethoxy-phenyl) | 174–5 | 52 | |
| 12 | 3,5-dimethoxy-benzimidic | 2-(3,5-dimethoxyphenyl) | 145–6 | 58 | |
| 13 | m-ethoxybenzimidic | 2-(m-ethoxyphenyl) | 166–7 | 71 | |
| 14 | m-propoxybenzimidic | 2-(m-propoxyphenyl) | 151–2 | 89 | |
| 15 | m-benzyloxybenzi- | 2-(m-benzyloxyphenyl) | 160–1 | 73 | |

-continued

| Example No. | A imidic acid ethyl ester | B -5H-s-triazolo [5,1-a]isoindole | M.p. °C | Overall Yield, % | M.p. of the intermediates, °C |
|---|---|---|---|---|---|
| | midic | | | | |
| 16 | 3,4-methylenedi-oxybenzimidic | 2-(3,4-methylenedi-oxyphenyl) | 194–5 | 64 | 218–20 |
| 17 | isonicotinimidic | 2-(4-pyridyl) | 205–7 | 65 | |
| 18 | m-trifluoromethyl-benzimidic | 2-(m-trifluoromethyl-phenyl) | 214–5 | 59 | 229–31 |
| 19 | m-fluorobenzimidic | 2-(m-fluorophenyl) | 171–2 | 73 | |
| 20 | 3,4-dimethylbenzimidic | 2-(3,4-dimethylphenyl) | 200–1 | 74 | |
| 21 | m-nitrobenzimidic | 2-(m-nitrophenyl) | 273–4 | 80 | 251–3 |
| 22 | p-dimethylamino-benzimidic | 2-(p-dimethylamino-phenyl) | 203–5 | 53 | |
| 23 | p-fluorobenzimidic | 2-(p-fluorophenyl) | 194–5 | 79 | |
| 24 | valerimidic acid | 2-n-butyl | 63–5 | 59 | |
| 25 | p-methoxybenzimidic | 2-(p-methoxyphenyl) | 157–8 | 85 | |

EXAMPLE 26

2-Amino-5H-s-triazolo[5,1-a]isoindole

A mixture of 26.2 g of N-aminophthalimidine hydrochloride (0.142 mole) and 6.25 g of cyanamide (0.149 mole) in 270 ml of anhydrous toluene are refluxed for two hours then, after cooling, the resulting solid precipitate is recovered by filtration. Yield, 31 g of the hydrochloride of 1-(2-phthalimidinyl)- guanidine. M.p. 269–70°C. An amount of 7.6 g (0.033 mole) of this latter compound is added to a solution of 1.5 g of 80% sodium hydride (0.05 mole) in 90 ml of ethanol and the mixture is refluxed for five hours. The solvent is distilled off in vacuo and the solid residue is taken up with water and the pH of the mixture is brought to 7 by addition of acetic acid. Extraction with dichloromethane and evaporation of the organic phase yields 4.5 g (78%) of the title product. M.p. 193–4°C (from ethanol).

EXAMPLE 27

2-Benzoylamino-5H-s-triazolo[5,1-a]isoindole

2-Amino-5H-s-triazolo[5,1-a]isoindole (3.45 g) and benzoic anhydride (5.43 g) in 45 ml of benzene are refluxed for 16 hours. After cooling to room temperature, the resulting solid precipitate is filtered and washed with aqueous sodium bicarbonate and water. Crystallization from ethanol affords 3.05 g (55%) of the title product which melts at 220–1°C.

EXAMPLE 28

5H-s-triazolo[5,1-a]isoindole

To a solution of 2 ml of 10% H₂SO₄ in 12 ml of water, a solution of 0.69 g (0.004 mole) of 2-amino -5H-s-triazolo[5,1-a]isoindole in 20 ml of water containing 4 ml of 10% H₂SO₄ is added. Under cooling to a 0–3°C, 8 ml of 0.5 N NaNO₂ is dropped into the solution and 7.8 ml of 50% H₃PO₂ is successively added. After heating to about 40°C for 30 minutes, the mixture is filtered and the filtrate is brought to pH 8 with Na₂CO₃. The aqueous phase is extracted several times with ethyl ether and the organic extract is evaporated to dryness. The residual crude product is purified by crystallization from isopropyl ether. Yield 0.32 g (50%). M.p. 116–7°C. The same compound may be obtained by heating at 140°C for 16 hours N-aminophthalimidine with an excess of formamide in the presence of a catalytic amount of piperidine acetate. Yield 63%.

EXAMPLE 29

2-Diacetylamino-5H-s-triazolo[5,1-a]isoindole

2-Amino-5H-s-triazolo[5,1-a]isoindole (12 g) is boiled for 4 hours in acetic anhydride. (120 ml). After distillation of the excess of the anhydride, the residue is crystallized from ethanol. Yield 16.15 g (90%). M.p. 174–6°C.

EXAMPLE 30

2-Acetamido-5H-s-triazolo[5,1-a]isoindole

2-Amino-5H-s-triazolo[5,1-a]isoindole (12.08 g) and acetic anhydride (8 ml) are boiled for one hour in 150 ml of benzene. After cooling, the solid precipitate is recovered on filter and then is crystallized from ethyl acetate. Yield 14.35 g (97%). M.p. 258–9°C.

EXAMPLE 31

2-Ethylamino-5H-s-triazolo[5,1-a]isoindole

2-Acetamido-5H-s-triazolo[5,1-a]isoindole is reduced with lithium aluminum hydride at 0–10°C in dimethoxyethane. Yield 60%. M.p. 150–2°C (isopropyl ether).

EXAMPLE 32

2-Thioureido-5H-s-triazolo[5,1-a]isoindole

To a solution of 8.6 g of 2-amino-5H-triazolo[5,1-a]isoindole (0.05 mole) in 200 ml of acetonitrile, a solution of 6.6 g of carbethoxyisothiocyanate (0.05 mole) in 40 ml of acetonitrile is added at about 50°C. The mixture is allowed to stand at room temperature for about two hours then, after boiling for one hour, is cooled to about 5°C. The resulting solid precipitate is recovered on the filter, yielding 11.85 g (78.3%) of 2-carbethoxythioureido-5H-s-triazolo[5,1-a]isoindole. M.p. 188-90°C from ethanol. An amount of 7.85 g of 2-carbethoxythioureido-5 -triazolo[5,1-a]isoindole is heated at 90°C for half an hour in 240 ml of 5% naOH. The mixture is chilled and neutralized with dilute HC1. The crude 2-thioureido-5H-s-triazolo[5,1-a]isoindole is filtered and crystallized from dimethylformamide. Yield 5.45 g (91%). M.p. 283–5°C (dec).

EXAMPLE 33

2-Sulfhydryl-5H-s-triazolo[5,1-a]isoindole

To 22.1 g of N-aminophthalimidine hydrochloride (0.12 mole), 11.65 g of potassium thiocyanate (0.12 mole) in 50 ml of water is added at room temperature and, after two hours, the mixture is evaporated to dryness. The solid residue is gradually heated to about 140°C in an open vessel. After 20 minutes at 140°C, the reaction mixture is cooled and the crude product is crystallized from 70% ethanol, giving 22 g of N-thioureidophthalimidine, m.p. 226–8°C. An amount of 19 g of N-thioureidophthalimidine (0.0916 mole) is refluxed for 40 hours with 5.5 g of 80% sodium hydride (0.183 mole) in 350 ml of isopropanol. Evaporation of the solvent gives a solid which is taken up with water and the solution is acidified to pH 5 with acetic acid. The solid so precipitated is recovered on the filter and recrystallized from 80% ethanol. Yield 9.5 g (55%). M.p. 259–61°C.

EXAMPLE 34

2-(m-Aminophenyl)-5H-s-triazolo[5,1-a] isoindole 2-(m-Nitrophenyl)-5H-s-triazolo[5,1-a] isoindole (7.7 g) is hydrogenated at atmospheric pressure and at room temperature in the presence of 2 g of 10% Pd on charcoal and 8 ml of 15% ethanolic hydrogen chloride. The product so obtained is purified by crystallization from ethanol. Yield 6.1 g (89%) of the title product which melts at 163–4°C.

EXAMPLE 35

2-(m-Acetamidophenyl)-5H-s-triazlo[ 5,1-a]isoindole

The title compound is obtained by refluxing for 3 hours 1.75 g of 2-(m-aminophenyl)-5H-s-triazolo[ 5,1-a]isoindole with 0.8 ml of acetic anhydride in 50 ml of benzene. After evaporation of the solvent the product is crystallized from ethanol; yield 1.65 g (81%); m.p. 254–5°C.

EXAMPLE 36

2-(m-Dimethylaminophenyl)-5H-s-triazolo[ 5,1-a]isoindole 2-(m-Aminophenyl)-5H-s-triazolo[5,1-a] isoindole (4g) is stirred for 3 hours at room temperature, then refluxed for ten hours with 4 ml of methyl iodide in 45 ml of methanol in the presence of 10.12 g of potassium carbonate. The solvent is evaporated under vacuum and residue is washed with water and crystallized from ethyl acetate to give 3.5 g (79%) of the title product. M.p. 233–7°C.

EXAMPLE 37

2-(3-Hydroxyphenyl)-5H-s-triazolo[5,1-a] isoindole 2-(3-Benzyloxyphenyl)-5H-s-triazolo[5,1-a] isoindole (17 g) is suspended in 500 ml of ethanol and hydrogenated at atmospheric pressure and room temperature in the presence of 3 g of 10% Pd on charcoal. After addition of 500 ml of methylene chloride, the catalyst is filtered off and the solution is concentrated to dryness. The title product is purified by crystallization from dioxane. Yield 10.68 g (85.7%); m.p. 251–2°C.

EXAMPLE 38

2-(3-Ethoxyphenyl)-5H-s-triazolo[5,1-a] isoindole 2-(3-Hydroxyphenyl)-5H-s-triazolo[5,1-a] isoindole (1.25 g, 0.05 mole) is added to 20 ml of ethanol containing one equivalent proportion of sodium ethoxide. To this mixture is added 0.49 ml (0.06 mole) of ethyl iodide in 5 ml of ethanol. After stirring for one hour at room temperature, a further amount of 0.49 ml of ethyl iodide is added. After refluxing for one hour the solvent is distilled off and the residue is washed with water and extracted with dichloromethane. Evaporation of the solvent and crystallization of the residue from ethanol gives 1 g (73%) of the title product, m.p. 166°–7° C.

EXAMPLES 39–42

By alkylating 2-(3-hydroxyphenyl)-5H-s-triazolo[5,1-a]isoindole with one of the reagents identified under column A according to the procedure described in Example 38, the compounds identified under column B are obtained.

| Example | A | B -5H-s-triazolo-[5,1-a]isoindole | M.p., °C |
|---|---|---|---|
| 39 | methyl iodide | 2-(m-methoxyphenyl)- | 132–3 |
| 40 | propyl bromide | 2-(m-propoxyphenyl)- | 151–2 |
| 41 | chloroacetic acid | 2-(m-carboxymethoxyphenyl) | 311–3 |
| 42 | ethyl chloroacetate | 2-(m-carbethoxymethoxyphenyl) | 125–6 |

EXAMPLE 43

2-Ureido-5H-s-triazolo[5,1-a]isoindole

2-Thioureido-5H-s-triazolo[5,1-a]isoindole (1.15 g, 0.005 mole) is suspended in 20 ml of 2% aqueous sodium hydroxide and 2.3 ml of 36% $H_2O_2$ (0.024 mole) is added at 40°–45° C. After 15 minutes, the mixture is heated for 5 minutes at 80° C then, after cooling and neutralizing with dilute hydrochloric acid, the resulting solid precipitate is recovered by filtration and is purified by crystallization from 60% ethanol. Yield 0.83 g; m.p. 261°–3° C.

EXAMPLE 44

2-Dimethylamino-5H-s-triazolo[5,1-a]isoindole

2-Amino-5H-s-triazolo[5,1-a]isoindole (4.3 g, 0.025 mole) is dissolved in 100 ml of ethanol and, after addition of 8 ml of 40% formaldehyde and 30 ml of acetic acid, the mixture is hydrogenated at room temperature and at a pressure of 5 atmospheres in the presence of one gram of 10% Pd on charcoal. After filtration of the catalyst, the solvent is evaporated off and the solid residue is crystallized from 200 ml of isopropyl ether. Yield 4.18 g (83%); m.p. 164°–6° C.

EXAMPLE 45

7,8-Dimethoxy-2-(m-methoxyphenyl)-5H-s-triazolo[5,1-a]isoindole

The compound is prepared according to the procedure of Example 1 from N-amino-5,6-dimethoxyphthalimidine (m.p. 163°–4° C) and m-methoxybenzimidic acid ethyl ester; m.p. 186°–7° C.

EXAMPLE 46

8-Methoxy-2-(m-methoxyphenyl)-5H-s-triazolo[5,1-a]isoindole

The compound is prepared according to the procedure of Example 1 from N-amino-6-methoxyphthalimidine (m.p. 177°–9° C) and m-methoxybenzimidic acid ethyl ester; m.p. 136°–8° C.

EXAMPLE 47

7-Methoxy-2-(m-methoxyphenyl)-5H-s-triazolo[5,1-a]isoindole

The title compound is prepared from N-amino-5-methoxyphthalimidine (m.p. 164–6 ° C) and m-methoxybenzimidic acid ethyl ester. M.p. 166°–7° C.

EXAMPLE 48

7-Chloro-2-(m-methoxyphenyl)-5H-s-triazolo[5,1-a]isoindole

The title compound is prepared from N-amino-5-chlorophthalimidine (m.p. 199°–201° C) and m-methoxybenzimidic acid ethyl ester. M.p. 229°–30° C.

EXAMPLE 49

8-Chloro-2-)m-methoxyphenyl)-5H-s-triazolo[5,1-a]isoindole

The title compound is prepared from N-amino-6-chlorophthalimidine (m.p. 170°–2° C) and m-methoxybenzimidic acid ethyl ester. M.p. 213°–4° C.

EXAMPLES 50–54

The following compounds are prepared by reacting N-aminophthalimidine substituted in the aromatic ring with benzimidic acid ethyl ester.

50) 7,8-Dimethoxy-2-phenyl-5H-s-triazolo[5,1-a]isoindole. M.p. 208°–9° C.
51) 8-Methoxy-2-phenyl-5H-s-triazolo[5,1-a]isoindole. M.p. 171°–3° C.
52) 7-Methoxy-2-phenyl-5H-s-triazolo[5,1-a]isoindole. M.p. 182°–4° C.
53) 7-Chloro-2-phenyl-5H-s-triazolo[5,1-a]isoindole. M.p. 225°–6° C.
54) 8-Chloro-2-phenyl-5H-s-triazolo[5,1-a]isoindole. M.p. 234°–6° C.

By operating according to the procedures of the foregoing examples, the following compounds are prepared:

2-Diethylamino-5H-s-triazolo[5,1-a]isoindole
2-Propylamino-5H-s-triazolo[5,1-a]isoindole
2-Butylamino-5H-s-triazolo[5,1-a]isoindole
2-Dibutylamino-5H-s-triazolo[5,1-a]isoindole
2-Benzoylthioureido-5H-s-triazolo[5,1-a]isoindole
2-(2-Pyridyl)-5H-s-triazolo[5,1-a]isoindole
2-(2,6-Dimethyl-4-pyridyl)-5H-s-triazolo[5,1-a]isoindole
2-(2-Methyl-4-pyridyl)-5H-s-triazolo[5,1-a]isoindole
2-(m-Ethylphenyl)-5H-s-triazolo[5,1-a]isoindole
2-(m-Isobutylphenyl)-5H-s-triazolo[5,1-a]isoindole
2-(m-Allyloxyphenyl)-5H-s-triazolo[5,1-a]isoindole
2-(m-Propargyloxyphenyl)-5H-s-triazolo[5,1-a]isoindole
2-(m-Cyclopropoxyphenyl)-5H-s-triazolo[5,1-a]isoindole
2-(m-Isopropoxyphenyl)-5H-s-triazolo[5,1-a]isoindole
2-(m-Cyclobutoxyphenyl)-5H-s-triazolo[5,1-a]isoindole
2-(m-Cyclopentyloxyphenyl)-5H-s-triazolo[5,1-a]isoindole
2-(m-Butoxyphenyl)-5H-s-triazolo[5,1-a]isoindole
2-[m-(tert-Butoxyphenyl)]-5H-s-triazolo[5,1-a]isoindole
2-(m-Pentyloxyphenyl)-5H-s-triazolo[5,1-a]isoindole
2-(m-Cyclohexyloxyphenyl)-5H-s-triazolo[5,1-a]isoindole
2-(m-Isoamyloxyphenyl)-5H-s-triazolo[5,1-a]isoindole

EXAMPLE 55

2-Phenyl-5H-s-triazolo[5,1-a]isoindole

3-Phenyl-5-(o-bromomethylphenyl)-s-triazole hydrobromide (41 g) is added to a solution of 6.55 g of 80% sodium hydride in 525 ml of ethanol at about 20° C. The obtained mixture is refluxed for about two hours, then the solvent is distilled off. The crude residue is extracted with 620 ml of benzene and the organic phase is evaporated, yielding 18.6 g of 2-phenyl-5H-s-triazolo[5,1-a]isoindole, which is purified by crystallization from ethanol. M.p. 156°–8° C. The starting compound 3-phenyl-5-(o-bromomethylphenyl)-s-triazole hydrobromide is obtained by evaporation of a solution of 3-phenyl-5-(o-hydroxymethylphenyl)-s-triazole in acetic acid saturated with hydrogen bromide. M.p. 193°–5° C.

EXAMPLE 56

2-(m-Chlorophenyl)-5H-s-triazolo[5,1-a]isoindole

The title compound is prepared according to the procedure of Example 55, starting from 3-(m-chlorophenyl)-5-(o-bromomethylphenyl)-s-triazole hydrochloride (M.p. 221° C).

EXAMPLE 57:
A vial for injectable use is prepared containing 2-(m-Methoxyphenyl)-5H-s-triazolo[5,1-a]-
isoindole 30 mg
Benzyl benzoate 300 mg
Sesame oil q.s. to 2 ml.

EXAMPLE 58:
A vial for injectable use is prepared containing 2-(m-Propoxyphenyl)-5H-s-triazolo[5,1-a]-
isoindole 35 mg
Benzyl alcohol 100 mg
Peanul oil q.s. to 2 ml.

EXAMPLE 59:
A vial for injectable use is prepared containing 2-(m-Ethoxyphenyl)-5H-s-triazolo[5,1-a]-
isoindole 35 mg
Benzyl alcohol 100 mg
Castor oil q.s. to 2 ml.

EXAMPLE 60:
A capsule is prepared containing 3-Phenyl--5H-s-triazolo[5,1-a]-
isoindole 50 mg
Talc 5 mg
Sodium carboxy-
methylcellulose 5 mg
Starch q.s. to 150 mg.

EXAMPLE 61:
100 ml Of solution of oral use are prepared from 2-(p-Chlorophenyl)-5H-s-triazolo[5,1-a]-
isoindole 800 mg
Hydroxyethyl-
cellulose 0.5 mg
Saccharine 17 mg Water, q.s. to 100 ml.

We claim:
1. A compound of the formula

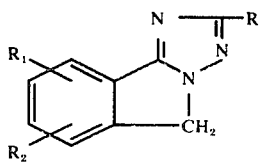

wherein R is selected from hydrogen, amino, lower alkyl amino, di-lower alkyl amino, lower alkanoylamino, di-lower alkanoylamino, benzoylamino, ureido, thioureido, carbethoxythioureido, benzoylthioureido, sulfhydryl, lower alkyl, trifluoromethyl, phenyl, pyridyl, methylpyridyl, dimethylpyridyl and phenyl having one to three substituents independently selected from lower alkyl, lower alkoxy, lower alkenyloxy, lower alkynyloxy, methylenedioxy, halo, trifluoromethyl, hydroxy, cyclopropyloxy, cyclobutyloxy, cyclopentyloxy, cyclohexyloxy, benzyloxy, carboxymethoxy, carbo(lower alkoxy)methoxy, amino, lower alkylamino, di-lower alkylamino, lower alkanoylamino and nitro; and $R_1$ and $R_2$ each independently represents hydrogen, chloro or lower alkoxy.

2. A compound as claimed in claim 1 wherein R is phenyl or substituted phenyl of the formula

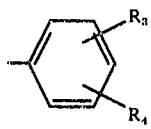

wherein one of the substituents $R_3$ and $R_4$ is located in the 3- or 4-position of the phenyl radical and represents lower alkyl, lower alkoxy, lower alkenyloxy, lower alkynyloxy, di-lower alkylamino, halo, trifluoromethyl, hydroxy, cyclopropyloxy, cyclobutyloxy, cyclopentyloxy, cyclohexyloxy or benzyloxy and the other substituent is hydrogen, lower alkoxy or halo; or wherein $R_3$ and $R_4$ taken together represent methylenedioxy.

3. A compound as claimed in claim 1 wherein R is lower alkyl, lower alkylamino, di-lower alkylamino, lower alkanoylamino, di-lower alkanoylamino, benzoylamino, ureido or sulfhydryl; and $R_1$ and $R_2$ are both hydrogen.

4. A compound as claimed in claim 1 wherein R is pyridyl, methylpyridyl or dimethylpyridyl; and $R_1$ and $R_2$ are both hydrogen.

5. A compound as claimed in claim 1 wherein R is thioureido or carbethoxythioureido; and $R_1$ and $R_2$ are both hydrogen.

6. The compound of claim 1 which is 2-phenyl-5H-s-triazolo[5,1-a]isoindole.

7. The compound of claim 1 which is 2-(m-methoxyphenyl)-5H-s-triazolo[5,1-a]isoindole.

8. The compound of claim 1 which is 2-(m-ethoxyphenyl)-5H-s-triazolo[5,1-a]isoindole.

9. The compound of claim 1 which is 2-(m-propoxyphenyl)-5H-s-triazolo[5,1-a]isoindole.

10. The compound of claim 1 which is 2-(3,4-methylenedioxyphenyl)-5H-s-triazolo[5,1-a]isoindole.

11. The compound of claim 1 which is 8-methoxy-2-(m-methoxyphenyl)-5H-s-triazolo[5,1-a]isoindole.

12. The compound of claim 1 which is 8-chloro-2-phenyl-5H-s-triazolo[5,1-a]isoindole.

13. The compound of claim 1 which is 8-chloro-2-(m-methoxyphenyl)-5H-s-triazolo[5,1-a]isoindole.

14. The compound of claim 1 which is 8-methoxy-2-phenyl-5H-s-triazolo[5,1-a]isoindole.

15. The compound of claim 1 which is 7-chloro-2-(m-methoxyphenyl)-5H-s-triazolo[5,1-a]isoindole.

16. The compound of claim 1 which is 2-(m-chlorophenyl)-5H-s-triazolo[5,1-a]isoindole.

17. A method for terminating pregnancy in an impregnated female animal which comprises administering to said animal an effective amount of a compound of formula I

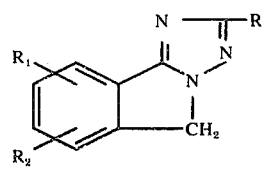

wherein R is phenyl or substituted phenyl of the formula

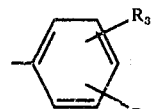

wherein one of the substituents $R_3$ and $R_4$ is located in the 3- or 4-position of the phenyl radical and represents a lower alkyl, lower alkoxy, lower alkenyloxy, lower alkynyloxy, di-lower alkylamino, halo, trifluoromethyl, hydroxy, cyclopropyloxy, cyclobutyloxy, cyclopentyloxy, cyclohexyloxy or benzyloxy group and the other is a hydrogen, lower alkoxy or halo group; or wherein $R_3$ and $R_4$ taken together represent methylenedioxy.

18. A pharmaceutical composition for terminating pregnancy in an impregnated female animal comprising as the active ingredient an effective amount of a compound of formula I

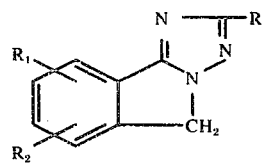

wherein R is phenyl or substituted phenyl of the formula

wherein one of the substituents $R_3$ and $R_4$ is located in the 3- or 4-position of the phenyl radical and represents a lower alkyl, lower alkoxy, lower alkenyloxy, lower alkynyloxy, di-lower alkylamino, halo, trifluoromethyl, hydroxy, cyclopropyloxy, cyclobutyloxy, cyclopentyloxy, cyclohexyloxy or benzyloxy group and the other is a hydrogen, lower alkoxy or halo group; or wherein $R_3$ and $R_4$ taken together represent methylenedioxy; in combination with a pharmaceutically-acceptable carrier.

* * * * *